(12) United States Patent
Hutel et al.

(10) Patent No.: US 11,867,783 B2
(45) Date of Patent: Jan. 9, 2024

(54) APPARATUS AND METHOD FOR ANALYSING FUNCTIONAL MRI DATA

(71) Applicant: King's College London, London (GB)

(72) Inventors: Michael Hutel, London (GB); Sebastien Ourselin, London (GB)

(73) Assignee: King's College London, London (GB)

( * ) Notice: Subject to any disclaimer, the term of this patent is extended or adjusted under 35 U.S.C. 154(b) by 617 days.

(21) Appl. No.: 17/058,714

(22) PCT Filed: May 31, 2019

(86) PCT No.: PCT/GB2019/051495
§ 371 (c)(1),
(2) Date: Nov. 25, 2020

(87) PCT Pub. No.: WO2019/229454
PCT Pub. Date: Dec. 5, 2019

(65) Prior Publication Data
US 2021/0208224 A1 Jul. 8, 2021

(30) Foreign Application Priority Data
May 31, 2018 (GB) .................................. 1808904

(51) Int. Cl.
*G06K 9/00* (2022.01)
*G01R 33/48* (2006.01)
(Continued)

(52) U.S. Cl.
CPC ........ *G01R 33/4806* (2013.01); *A61B 5/4064* (2013.01); *G01R 33/5608* (2013.01);
(Continued)

(58) Field of Classification Search
CPC .......................................... G06T 2207/10088
See application file for complete search history.

(56) References Cited

U.S. PATENT DOCUMENTS

| 2009/0318794 A1* | 12/2009 | DeCharms | ........... A61B 5/7282 |
| | | | 600/410 |
| 2011/0028827 A1* | 2/2011 | Sitaram | .................. A61B 5/055 |
| | | | 600/410 |

(Continued)

OTHER PUBLICATIONS

Costantini I, Deriche R, Deslauriers-Gauthier S. An Anisotropic 4D Filtering Approach to Recover Brain Activation From Paradigm-Free Functional MRI Data. Front Neuroimaging. 2022 (Year: 2022).*

(Continued)

*Primary Examiner* — Hadi Akhavannik
(74) *Attorney, Agent, or Firm* — Hamilton, Brook, Smith & Reynolds, P.C.

(57) ABSTRACT

A system and method are provided for analysing a functional magnetic resonance imaging (MRI) scan representing a time-sequence, comprising t time points, of images comprising v voxels, where each scan can be represented by a data matrix $X \in \mathbb{R}^{t \times v}$. The method comprises modelling the scan data X as the convolution of neural activation time courses $N \in \mathbb{R}^{t \times v}$ and a haemodynamic filter $\Psi$, and performing an inverse operation to estimate N from X and $\Psi$. The method further compasses decomposing the neural activation time courses N into multiple brain network components by representing N as the product of a first matrix H defining, for each component, a spatial map of the voxels belonging to that component, and a second matrix W defining, for each component, the time sequence of activation of that component during the scan. In other implementations, the matrix decomposition may be performed before the deconvolution.

19 Claims, 6 Drawing Sheets

(51) Int. Cl.
 G06T 7/30 (2017.01)
 A61B 5/00 (2006.01)
 G01R 33/56 (2006.01)
 G01R 33/565 (2006.01)
 G06T 7/00 (2017.01)
 G06T 11/00 (2006.01)

(52) U.S. Cl.
 CPC ...... *G01R 33/56509* (2013.01); *G06T 7/0014* (2013.01); *G06T 7/30* (2017.01); *G06T 11/006* (2013.01); *G06T 2207/10088* (2013.01); *G06T 2207/20081* (2013.01); *G06T 2207/30016* (2013.01)

(56) References Cited

U.S. PATENT DOCUMENTS

| | | | | |
|---|---|---|---|---|
| 2013/0211238 | A1* | 8/2013 | DeCharms | A61B 5/4848 600/407 |
| 2014/0316248 | A1* | 10/2014 | deCharms | A61B 5/7282 600/411 |
| 2014/0335489 | A1* | 11/2014 | DeCharms | A61B 5/4064 434/236 |
| 2017/0311803 | A1* | 11/2017 | Hirsch | A61B 5/0075 |

OTHER PUBLICATIONS

Hütel M, Antonelli M, Melbourne A, Ourselin S. Hemodynamic matrix factorization for functional magnetic resonance imaging. Neuroimage. 2021 (Year: 2021).*

Karahanoglu F. I., et al., "Total activation: fMRI deconvolution through spatio-temporal regularization," Neuroimage, Elsevier, Amsterdam, NL, vol. 73, No. 4 (2013).

Hütel M., et al., "Neural Activation Estimation in Brain Networks During Task and Rest Using BOLD-fMRI", International Conference On Computer Analysis Of Images And Patterns. Caip 2017: Computer Analysis Of Images And Patterns; [Lecture Notes In Computer Science; Lect. Notes Computer], Springer, Berlin, Heidelberg, pp. 215-222 (2018).

Prando, et al., "Estimating effective connectivity in linear brain network models", Arxiv.Org, Cornell University Library (2017).

Sreenivasan K. R., et al., "Nonparametric Hemodynamic Deconvolution of fMRI Using Homomorphic Filtering", IEEE Transactions On Medical Imaging, vol. 34, No. 5, pp. 1155-1163 (2014).

Guo-Rong W., et al., "A blind deconvolution approach to recover effective connectivity brain networks from resting state fMRI data", Medical Image Analysis, vol. 17, No. 3, pp. 365-374 (2013).

International Search Report for International Application No. PCT/GB2019/051495, entitled "Apparatus and Method For Analysing Functional MRI Data," dated Aug. 28, 2019.

Brouwer, T., et al., "Fast bayesian non-negative matrix factorisation and tri-factorisation," arXiv preprint arXiv (2016).

Cichocki, A. at al., "Fast local algorithms for large scale nonnegative matrix and tensor factorizations," IEICE transactions on fundamentals of electronics, communications and computer sciences, 92(3):708-721 (2009).

Daubechies, I., et al, "Independent component analysis for brain fmri does not select for independence," Proceedings of the National Academy of Sciences, 106(26):10415-10422 (2009).

Glorot, X., et al. , "Understanding the difficulty of training deep feedforward neural networks," In Proceedings of the Thirteenth International Conference on Artificial Intelligence and Statistics, pp. 249-256 (2010).

Gordon, E. M., et al. "Precision functional mapping of individual human brains," Neuron, 95(4):791-807 (2017).

Kanagal, B., et al., "Rank selection in low-rank matrix approximations: A study of cross-validation for nmfs," In Proc Conf Adv Neural Inf Process, vol. 1, pp. 10-15 (2010).

Schmidt, M. N., et al. "Bayesian nonnegative matrix factorization," In International Conference on Independent Component Analysis and Signal Separation, pp. 540-547 (2009).

Logothetis, N. K., et al, "Neurophysiological investigation of the basis of the fmri signal," Nature, 412(6843):150-157 (2001).

Logothetis, N. K., et al. "Interpreting the bold signal," Annu. Rev. Physiol., 66:735-769 (2004).

Orfanos, D. P., et al., "The brainomics/localizer database," NeuroImage, 144:309-314 (2017).

Pinel, P., et al., "Genetic variants of foxp2 and kiaa0319/ttrap/them2 locus are associated with altered brain activation in distinct language-related regions." Journal of Neuroscience, 32(3):817-825 (2012).

Pinel, P., et al., "Fast reproducible identification and large-scale databasing of 295 individual functional cognitive networks," BMC neuroscience, 8(1):91 (2007).

* cited by examiner

APPARATUS AND METHOD FOR ANALYSING FUNCTIONAL MRI DATA

This application is the U.S. National Stage of International Application No. PCT/GB2019/051495, filed on May 31, 2019, which designates the U.S., published in English, and claims priority under 35 U.S.C. § 119 or 365(c) to Great Britain Application No. 1808904.5, filed on May 31, 2018. The entire teachings of the above applications are incorporated herein by reference.

FIELD

The present application relates to an apparatus and method for analysing magnetic resonance imaging (MRI) data, in particular to identify brain (e.g. cortical) networks.

BACKGROUND

Functional Magnetic Resonance Imaging (fMRI) is a key neuroimaging technique which is widely used for brain studies. One type of fMRI measures neuronal activity by detecting changes in the level of blood oxygenation in different parts of the brain (termed the haemodynamic response) and is referred to as blood-oxygen-level dependent (BOLD) fMRI. A high level of blood oxygenation is generally associated with increased blood flow (perfusion), which in turn is associated with neuronal activity. Accordingly, fMRI can be used to obtain a time-dependent, spatial representation of neuronal activity. The potential of fMRI to measure changes in functional cortical networks means that it is well-suited to complement local structural information provided by other MRI techniques.

BOLD fMRI is frequently used in studies of the brain to allow the identification and analysis of eloquent regions of the cortex (cortical areas that are consistently related to particular functionality). In this context, a brain network represents a collection or pattern of brain regions that show correlated activity. For example, a network may represent a set of brain regions that undergo activity simultaneously or in a certain time-coordinated sequence. Any given region of the brain may belong to zero, one, or multiple such networks.

One problem with BOLD fMRI is that the signal-to-noise ratio (SNR) tends to be relatively low, hence individual BOLD fMRI images contain a significant amount of noise. In principle this noise problem could be addressed by lengthening the exposure time, however it is difficult as well as expensive in practice for a single individual subject to spend a very long period of time in an MRI machine. Accordingly, large cohort studies involving a relatively high number of subjects are often used to help reduce noise; such studies also support investigations of variation across the population of individuals within the cohort.

The most common experimental approach in BOLD fMRI is to design task experiments that stimulate individual brain networks to cause increased local neuronal activity and changes in local blood flow. A binary function representing neural activity comprises onset and duration of the task. In other words, the binary function is on if the corresponding brain network is currently active, or off otherwise. This binary function may then be convolved with a haemodynamic response function (HRF), which relates neural activity to haemodynamic changes such as may be imaged using BOLD fMRI. The temporal regressor resulting from this convolution may be used in a General Linear Model (GLM), a mass univariate approach, to obtain a statistical parametric mapping (SPM) that shows how related individual voxels are to the given task.

In a pioneering study by [Logothetis et al., 2001], monkeys viewed checkerboard patterns in an MRI scanner while measurements of neuronal activity and BOLD signal change in their visual cortex were recorded simultaneously. This study was the first to show the intrinsic link between increased neural activity and BOLD signal increase, as well as the validity of the task-fMRI GLM. Since then, the relationship between the haemodynamic response (HR) and neuronal activity in task engagements [Logothetis and Wandell, 2004] has been extensively studied, mainly in animal models. Our current understanding is that the BOLD signal increase represents local field potentials (LFP), which are the summation of post-synaptic electric potentials from adjacent neuron populations. On the basis of this established link between neuronal activity and BOLD signal, several task experiments have been developed to map out underlying functional systems in humans.

By contrast, ongoing spontaneous neural activity from task-free fMRI experiments has been found to organize into so called resting-state networks (RSN) of intrinsic functional connectivity. In contrast to task-fMRI, matrix decomposition strategies have been used to study this intrinsic functional connectivity by extracting salient components H, from the data, X, subject to certain statistical assumptions. The fundamental problem is the decomposition of $X=WH$ so that the individual components of H have desirable properties. A spectrum of machine learning techniques as been proposed to produce H and W but these techniques do not model the relation between underlying neuronal activity and spontaneous BOLD signal fluctuations.

Previous work, see for example, US 2005/0215884, in identifying brain networks using BOLD fMRI has mainly relied upon Independent Component Analysis (ICA) to obtain these resting-state brain networks in individual subjects. However, ICA has several undesirable properties in the domain of fMRI. First, it imposes a strong hypothesis-driven model, which describes the value distribution of a component by a generalized Gaussian distribution (Daubechies et al., 2009). However, currently used ICA implementations in fMRI, such as FastICA (see https://en.wikipedia.org/wiki/FastICA), have produced sparse solutions (Daubechies et al., 2009) which may not fit well with the underlying assumed generalized Gaussian model. Second, ICA only delivers a point estimate of the underlying sources.

Last, and perhaps most importantly, as noted above, fMRI scans are noisy. Wide Gaussian smoothing kernels are typically applied as a preprocessing step to increase signal to noise ratio (SNR) and therefore these ultimately influence the subsequent ICA results. However, the haemodynamic response has varying spatial smoothness across brain regions. Accordingly, it is difficult to justify a fixed spatial smoothness with a Gaussian kernel. In addition, such spatial smoothing has a further disadvantage in the form of partial-volume effects at both the intra- and inter-subject level. A partial volume effect typically arises from a lack of imaging resolution compared with the sizing of anatomical features, such that the signal from different tissue types is mixed within an individual voxel. This may cause noise components to be structured, with a risk of confusion as a functional brain network and/or a systematic bias in the assessment of the functional brain networks.

The primary intra-subject partial volume effect is the smoothing of cardiac and respiratory noise fluctuations present in cerebrospinal fluid (CSF) and white matter tissue into blood oxygenation changes present in gray matter tissue. Unique subject network representation is therefore lost or compromised. The inter-subject partial volume effect causes an anatomical bias on functional connectivity and is especially significant when comparing atrophied brains or brains with tumour resection with healthy brains. Thus atrophied brain regions are more likely to be contaminated by physiological noise due to the changed ratio of CSF to gray matter. An obtained group difference might therefore be more likely to reflect the average difference in underlying tissue composition between cohorts than actual functional differences.

Thus although functional pathologies in resting-state networks have the potential to reveal much about brain disease, in current approaches, differences found in networks are often coupled to a variety of assumptions, such as the kernel size of the spatial smoothing operator, and therefore suffer from poor reproducibility. It would be helpful to improve on existing techniques for analysing fMRI data acquired in neuroimaging to determine networks of spontaneous brain function.

SUMMARY

The invention is defined in the appended claims.

A system and method are provided for analysing a functional magnetic resonance imaging (MRI) scan representing a time-sequence, comprising t time points, of images comprising v voxels, where each scan can be represented by a data matrix $X \in \mathbb{R}^{t \times v}$. The method comprises modelling the scan data X as the convolution of a neural activation time course $N \in \mathbb{R}_+^{t \times v}$ and a haemodynamic filter $\psi$, and performing an inverse operation to estimate N from X and $\psi$. The method further comprises decomposing the neural activation time course N into multiple brain network components by representing N as the product of a first matrix H defining, for each component, a spatial map of the voxels belonging to that component, and a second matrix W defining, for each component, the time sequence of activation of that component during the scan.

A system and method are also provided for analysing a functional magnetic resonance imaging (fMRI) scan representing a time-sequence, comprising t time points, of images comprising v voxels, where each scan can be represented by a data matrix $X \in \mathbb{R}^{t \times v}$. The method comprises decomposing the data matrix X into multiple brain network components by representing X as the product of a first matrix H defining, for each component, a spatial map of the voxels belonging to that component, and a second matrix W*, where W* is formed by convolving a haemodynamic filter $\psi$ with a third matrix N*, defining, for each component, the time sequence of activation of that component during the scan. The method further comprises performing an inverse operation to estimate N* from W*.

It will be understood that the first method and system set out above perform the inverse operation (e.g. a deconvolution) before the matrix decomposition, while the second method and system set out above perform the inverse operation after the matrix decomposition. Although these two techniques are largely equivalent from a mathematical perspective, it is believed that the latter technique may be slightly more effective for scans with higher noise, whereas the former technique may be slightly more effective for scans with lower noise. Some implementations may also potentially perform the inverse operation and the matrix decomposition together as part of a joint optimisation.

A given system or apparatus may support multiple techniques, i.e. being able to perform the inverse operation before, after and/or in conjunction with the matrix decomposition. Thus a system and method are also provided for analysing a functional magnetic resonance imaging (fMRI) scan representing a time-sequence, comprising t time points, of images comprising v voxels, where each scan can be represented by a data matrix $X \in \mathbb{R}^{t \times v}$. The method comprises modelling the scan data X as the convolution of a neural activation time course $N \in \mathbb{R}_+^{t \times v}$ and a haemodynamic filter $\psi$. The method further comprises performing an inverse operation with respect to $\psi$ and a matrix decomposition into multiple brain network components using a matrix H defining, for each component, a spatial map of the voxels belonging to that component, to derive for each component, the time sequence of activation of that component during the scan.

The approach described herein can be used in two different contexts, referred to as training and production respectively. Firstly, in a training phase when no prior information is available for a cohort of subjects, respective individual MRI scans are decomposed into a set of brain network components, each such component comprises a spatial map, representing the location of the component within the brain. A surrogate neural activity time course may be determined for each component (such neural activity is considered to be a surrogate in the sense that it reflects the activity of populations of neurons, rather than activity at the level of individual neurons; the former is clearly dependent on the latter, however, the exact form of the relationship, especially in quantitative rather than qualitative terms, is not fully understood at present). A deconvolution filter may be used, followed by performing a matrix decomposition, for determining the appropriate number of brain network components to represent the MRI scans of a given task (a particular task may involve activation of multiple different brain network components). As an example, the matrix decomposition may be a non-negative matrix factorization (NMF) and may use double singular value decomposition (NNDSVD) initialization or random initialization (or any other appropriate form of initialization).

Secondly, for a production phase when prior information is available for a cohort or single subject, this implies that the deconvolution filter ($T_A$) and the spatial maps (H) of the brain network components are already known. Accordingly, individual MRI scans can be transformed with the filter $T_A$ and compressed using the known spatial maps H to allow the respective surrogate neural activation time courses to be obtained very quickly (in effect, in real-time).

BRIEF DESCRIPTION OF THE DRAWINGS

Various implementations are described below by way of example only with reference to the following drawings.

DETAILED DESCRIPTION

1) Overview

Figure 1:
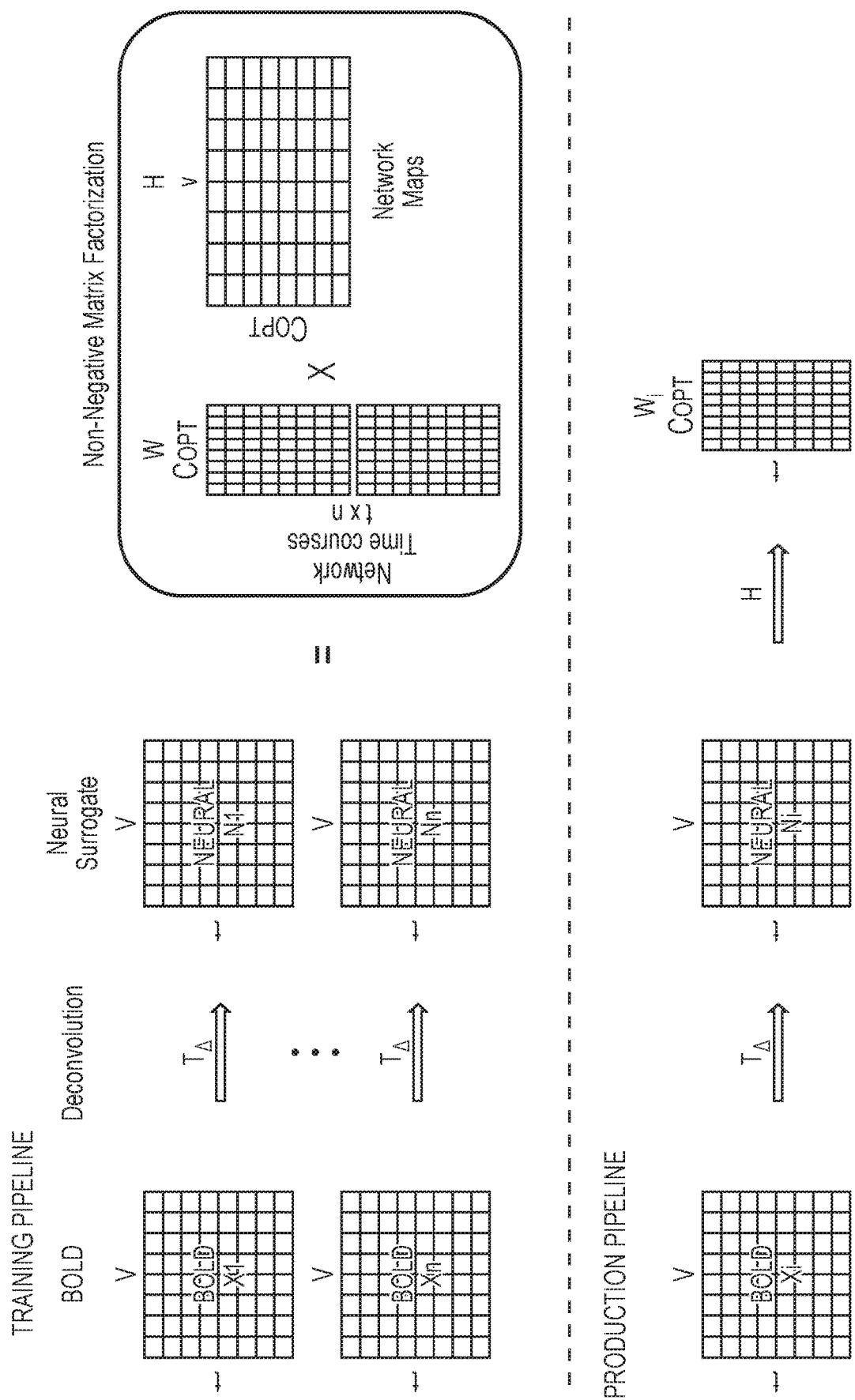
FIG. 1 is a schematic diagram representing an overview of the approach described herein, including both a training phase and production phase.

The brain comprises several functional neurophysiological brain networks whose up and down regulation in blood perfusion reflects changes in ongoing neuronal activity. These networks can be obtained from a BOLD-fMRI, but single subject BOLD-fMRI scans are low in SNR and also comprise structured noise components in addition to the brain networks of interest. The approach described herein includes a training phase to learn a mapping of BOLD signal fluctuations to underlying neural activity. The obtained transformations can be applied directly in a subsequent production phase to single subject BOLD-fMRI scans. Such a scan comprises a 4-D data-set, in which a succession of 3-D (volumetric) images is acquired over time to produce a data set having three spatial dimensions and one temporal dimension. The 3-D images, which are formed of voxels, may themselves be acquired as a sequence of 2-D (planar) images (also referred to as slices).

Individual components within a scan are either noise- or network-related. Network-related components are associated with known brain networks in a probabilistic manner. Sources are modelled as probabilistic maps to produce uncertainty estimates for these probabilities. This approach provides an identification of brain networks (network areas) that can reliably be reproduced in terms of cross-sectional and longitudinal position.

The approach described herein can be regarded as a minimalist technique that reduces the amount of preprocessing, reduces the number of model assumptions, and allows for a reliable separation of BOLD-related signal from BOLD-unrelated signal. The approach is based on a framework that includes: (i) a non-linear deconvolution operation that produces a novel filter that transforms BOLD signal into a surrogate for underlying neural activity, and (ii) a non-negative matrix factorization (NMF), see e.g. [Cichocki and Anh-Huy, 2009], that finds a compression of the data into functional networks. When this approach is applied to unseen subjects, it results in surrogate neural activation time courses (sequences) for respective brain networks. It is shown herein that this approach produces natural, unique and reproducible functional networks for individual subjects without imposing spatial constraints in model fitting or spatial smoothing during preprocessing.

2) Materials and Methods

Functional brain networks organize at different scales. The approach described herein provides two related techniques to infer neural activation at either a large network scale, such as corresponding to a functional brain network (one or more regions of the brain that act together for performing a particular function), or in individual voxels or atlas regions (regions or segments of the brain identified in one of the standard available cortical parcellations or segmentations, see for example: http://neuro.imm.dtu.dk/wiki/Harvard-Oxford_Atlas).

For a first technique, a Haemodynamic Deconvolution is provided that uses neural network machine learning techniques to map BOLD time courses to surrogate neural activation time courses. A BOLD-fMRI scan comprises a large amount of redundant information because of the high correlation among time courses of adjacent voxels, i.e. both spatial and temporal correlation. Therefore, a non-negative matrix factorization is used to find an efficient data compression of the obtained neural activation signals into associated functional networks. Each functional network obtained in this manner has two components: a spatial map (pattern) and a neuronal activity time course. The latter defines the timings when the former (i.e. all brain regions that lie within a given pattern) are on (active) or off (not active).

The second technique learns common spatial maps (functional brain networks) that compress the data in basis components that are a good data representation for capturing the correlation among adjacent voxels. The algorithm is trained on a representative cohort and brain stimulus (such as a particular task) to produce spatial basis functions that are used to infer underlying neural activity patterns in unseen individuals.

As described in more detail below, the two techniques set out above have been tested on both simulated and real imaging data with minimal preprocessing.

3) Functional Imaging Data

Simulated data from [Karahanoğlu et al., 2013] was used to compare results obtained by the approach described herein to results obtained using their method called Total Activation (TA) (i.e. the method of [Karahanoğlu et al., 2013]). The approach described herein was further evaluated using four imaging cohorts from different scanner manufacturers (Siemens, Phillips, Bruker, GE):

(i) The Midnight Scanning club (MSC) data (see https://openfmri.org/dataset/ds000224/) comprises 10 healthy adult subjects with six hours of task-free and five hours of task-based BOLD-fMRI experiments including motor tasks, incidental memory and a mixed design task acquired on a Siemens Trim Trio 3 Tesla scanner [Gordon et al., 2017].

(ii) The Brainomics data (see http://brainomics.cea.fr/localizer/dataset) comprises 94 subjects partially acquired on a Bruker and a Siemens 3 Tesla scanner with a very short and efficient BOLD-fMRI paradigm to localize several brain functions with various visual and auditory stimuli [Pinel et al., 2007, Pinel et al., 2012, Orfanos et al., 2017].

(iii) The Visual object recognition data (see https://openfmri.org/dataset/ds000105/) comprises 6 subjects acquired on a GE 3 Tesla scanner. Several visual stimuli are presented to obtain individual spatial activation patterns that encode (represent) either faces or objects in the ventral temporal cortex.

(iv) A dataset describing neural responses to naturalistic clips of animal behaviour in two different task contexts (https://openfmri.org/dataset/ds000233/) comprises 12 healthy subjects acquired on a Philips Intera Achieva scanner 3 Tesla.

4) Preprocessing BOLD-fMRI Data

Various preprocessing steps are performed on the acquired BOLD-fMRI data including volume realignment, in which, for each fMRI scan, the subject is motion realigned. Such motion may be caused, for example, by the breathing of the subject during the MRI scan. Thus for each 3-D image within the scan, the position and orientation of the brain are mapped to a common configuration, so as to remove (or at least reduce) the impact of any movement of the subject during the scan. A high-pass filter (0.01 Hz) is applied to remove slow scanner signal drift from BOLD time courses.

A bias-corrected structural image, brain parcelation and segmentation are derived from a separately obtained structural (anatomical) scan (such as T1). A co-registration between the functional scan and the structural scan can then be achieved to relate functional to anatomical brain regions. This in turn supports a normalization to be performed for each scan into MNI space, representing a standard, known, segmentation of the brain into anatomical structures (derived originally from work performed at the Montreal Neurological Institute). Each functional 4D scan (also referred to as a volume set) is reshaped into (represented as) a matrix $X \in \mathbb{R}^{t \times v}$ with t time points and v voxels, and each anatomical 3D image (volume) is reshaped into (represented as) a vector $m \in \mathbb{R}^v$ comprising v voxels. Anatomical masks can provide additional regularization to the algorithm, for example, a grey matter tissue probability mask can be used to lower the importance of other tissue types during the optimization.

5) Haemodynamic Deconvolution

BOLD-fMRI data X is modeled as the convolution of a surrogate neural activation time course $N \in \mathbb{R}_+^{t \times v}$ and a haemodynamic filter $\psi$. In other words, neurons activate/deactivate in accordance with a (binary) time sequence (course), and this neural activity in turn causes changes in blood oxygenation, as determined by the haemodynamic filter $\psi$ (which can be regarded as a form of transfer function). The changes in blood oxygenation are detected and recorded in the BOLD-fMRI data. An example of a suitable haemodynamic filter $\psi$ for use with the approach described herein is available at: https://en.wikipedia.org/wiki/Haemodynamic_response.

Convolution of multiple time courses with the haemodynamic filter $\psi$ can be efficiently formulated as a matrix multiplication with a Toeplitz matrix (see https://en.wikipedia.org/wiki/Toeplitz_matrix) $T_\psi \in \mathbb{R}^{t \times t}$ built from individual elements of the filter. We derive a non-linear deconvolution operation with a filter $T_A \in \mathbb{R}^{t \times t}$ to expose neural activation N from the observed BOLD time courses X (we can consider this as applying the inverse of the haemodynamic filter $\psi$ to recover (expose) the original neural activation sequences N from the observed BOLD time courses X. We can formulate an optimisation to perform the inverse filter operation within an optimization framework as:

$$\hat{X} = T_\psi N + b_1 = T_\psi f(T_A X) + b_1 \quad \text{(Eq 1)}$$

with f being a non-linear activation function f: $\mathbb{R} \to \mathbb{R}_+$. Bias $b_1 \in \mathbb{R}$ creates a negative baseline to compensate for negative time course values after the preprocessing described in the above pre-processing section (section 4). The parameters of the optimization framework are the filter $T_A$ and bias $b_1$, while filter $T_\psi$ is fixed and built from the generic haemodynamic response. Filter $T_A$ and bias $b_1$ are optimized under the following cost function:

$$arg\ min_{N,b_1} \|X - \hat{X}\|_2^2 \quad \text{(Eq 2)}$$

that minimises the l2 norm between the original data X and its reconstruction $\hat{X}$. Filter $T_A$ is initialized with values of a random Xavier initialization [Glorot and Bengio, 2010]. Bias $b_1$ is initialized with zeros. The back-propagation algorithm (chain rule) is applied to derive the corresponding gradient for the cost function. The gradient is optimized with the limited memory Broyden-Fletcher-Goldfarb-Shanno (L-BFGS) optimization scheme.

In general terms, equations (1) and (2) perform an optimisation in which a trial value of the inverse filter $T_A$ is utilised to transform (deconvolve) the observed data X into an estimate set of (surrogate) neural activity N, which is then transformed back into reconstructed MRI data $\hat{X}$ by convolving with the known haemodynamic filter $T_\psi$. The optimization finds an inverse filter $T_A$ such that the reconstructed data $\hat{X}$ closely matches the original observed data X, as per the minimisation of equation (2).

As discussed in more detail later, this determination of the inverse filter $T_A$ is implemented during an initial training phase by performing the above optimization across a set (cohort) of multiple scans to find the inverse filter $T_A$ that fits best across the set of multiple scans. This determined inverse filter $T_A$ can then be used directly on individual scans during a subsequent production phase to determine (estimate) N corresponding to the observations X from a given individual scan.

6) Haemodynamic Deconvolution Compression

The approach described above can be extended by finding a compression of the surrogate neural activation N=WH into $c \in N$ components described by two non-negative matrices $W \in \mathbb{R}_+^{t \times c}$ and $H \in \mathbb{R}_+^{c \times v}$. The matrix H defines the c components; for each component, the matrix H indicates which voxels are, or are not, in that component. The matrix W then defines, for each component, the time course (sequence) of when that component is, or is not, activated (it may be assumed in this model that all the neurons in a given component activate, or don't activate, together, i.e. in synchronism). In some implementations, H and/or W may be a binary matrix. In other implementations, H and/or W may be used, for example, to represent a probability that a given voxel v belongs to a given component, or that a given network (component) is activated at time t.

The optimization framework is altered to:

$$\hat{X} = T_\psi N + b_1 = T_\psi f(T_A X) + b_1 = T_\psi (WH) + b_1 \quad \text{(Eq 3)}$$

The optimization of equation (3) can be performed using any suitable non-negative matrix factorisation approach, see e.g. https://en.wikipedia.org/wiki/Non-negative_matrix_factorization. The only hyper-parameter to tune is the number of components c. One way of achieving this is to use cross-validation with a Gabriel holdout, as commonly used in non-negative matrix factorisation techniques as described in [Kanagal and Sindhwani, 2010] to determine an optimal c.

In general terms, the processing of equation (3) takes as inputs the observed data X and the inverse filter $T_A$ as determined in the previous section (and the associated bias $b_1$). The inverse filter $T_A$ is applied (by way of deconvolution) to the observed data X to produce an (estimated) observed N, and this observed N can then be compressed (factorised) into W and H. In particular, the optimization can be considered as determining the difference between (i) the observed N, and (ii) a value of N which is reconstructed from W and H, and seeking to find values of W and H that minimise this difference.

In the initial training phase, both W and H are unknown, and have to be determined by performing the above optimization across a set (cohort) of multiple scans. The cohort of scans used for training on W and H will typically be the same cohort as used for finding the inverse filter $T_A$, although this is not necessarily the case. For example, one possibility is that the training to determine the inverse filter $T_A$ is performed using a cohort that extends across multiple individuals, whereas the training on W and H may be performed on a set of scans specific to a given individual, e.g. if it is desired to investigate subject-specific brain networks.

In a subsequent production phase, the configuration of networks (H) determined from the training phase can be applied to individual scans, and hence the optimization (compression) only has to determine W, the time course for each respective known network (H). Such a determination of W is computationally fast, and generally can be completed in real-time (e.g. a few seconds).

7) Haemodynamic Deconvolution De-Noising

Some data cohorts may contain noise or other artefacts, such as extensive scanner and/or head motion, rendering voxel-wise neural surrogate analysis difficult or unreliable (or even impossible). In such circumstances, it may be beneficial to change the order of operators from that presented above to find an efficient compression of X directly into time course matrix $W^* \in \mathbb{R}^{t \times c}$ and spatial maps matrix $H^T \in \mathbb{R}_+^{v \times c}$, where we have used $W^*$ to represent the time course of the BOLD signal (distinguishing from W in equation (3), which is used to represent the time course of the surrogate neural signal). Such an optimization can again be performed using any suitable matrix factorisation approach, see e.g. https://en.wikipedia.org/wiki/Matrix_decomposition, or by using other techniques, such as independent component analysis (ICA), that are suitable for separating out noise components. (Note that this matrix factorisation does not have to be non-negative, since compressed BOLD time course are allowed to be negative, because the haemodynamic response function has an undershoot/deactivation part). The number of components c may be determined by using (for example) a cross-validation as mentioned above or information-theoretic measures, such as AIC (see https://en.wikipedia.org/wiki/Akaike_information_criterion), or BIC (see https://en.wikipedia.org/wiki/Bayesian_information_criterion).

After the compression, we may then apply the deconvolution filter ($T_A$) to the individual time courses $W^*$ to recover the surrogate neural signal $N^*$ (as defined below). The deconvolution filter ($T_A$) may only be applied to a subset of time courses $W^* \in \mathbb{R}^{t \times c_{BOLD}}$, with $c_{BOLD} < c$ (although in other cases, the deconvolution filter may be applied to all c networks if so desired). The subset may be selected, for example, by visual inspection, to contain just those components that appear to be less susceptible to instrumental effects (or for any other appropriate reason).

In the above circumstances, the optimization framework changes accordingly from equation 3 above to equation 3A below:

$$\hat{X} = \hat{W}^* H + b_1 = (T_\psi N^*) H + b_1 = (T_\psi f(T_A W^*)) H + b_1 \quad \text{(Eq 3A)}$$

where $\hat{W}^*$ represents the reconstruction of $W^*$. The benefit of such flipping (reversing the order) of the deconvolution and the compression operator is generally an increased noise tolerance with respect to corrupted data (a voxel-wise analysis is generally not obtained in such noisier circumstances, although an approximation of the activation sequence of individual voxels could if so desired be reconstructed from the activation sequences of the known network components).

Note that $N^*$ represents the surrogate neural activity at the level of components, rather than at the level of individual voxels (in contrast to N in equation (3), which is defined at the level of individual voxel). In this sense, $N^*$ is analogous to W in equation (3), and they are likely to be very similar to one another, albeit not identical because of different error terms resulting from the different calculation paths.

In general terms, equation (3A) involves determining (optimising) $W^*$ and H from the observed data X such that the reconstructed observations $\hat{X} = \hat{W}^* H$ minimise any difference between the observed data X and the reconstructed observations $\hat{X}$ (analogous to equation (2) above). This optimisation can be performed during the initial training phase, to determine both $W^*$ and H, and also during a subsequent production phase, with H already known, to determine $W^*$. In both phases, the surrogate neural activation signal $N^* \in \mathbb{R}_+^{t \times c_{BOLD}}$ can then be recovered by applying the deconvolution filter ($T_A$) to the determined $W^*$. During the training phase, the deconvolution filter ($T_A$) may be determined using the method described above based on equations (1) and (2). Alternatively, an analogous optimisation may be performed, in which a trial deconvolution filter is applied to $W^*$ to generate $N^*$, and then the known haemodynamic filter $T_\psi$ is applied to (convolved with) $N^* H$ to provide reconstructed data $\hat{X}$. And the optimisation finds the trial deconvolution filter which minimises the differences between the observed data X and the reconstructed data $\hat{X}$.

8) Probabilistic Haemodynamic Deconvolution Compression

One can take a probabilistic approach to performing the non-negative matrix factorization. As described above, this again represents a decomposition of $N \in \mathbb{R}^{t \times v}$ into latent matrices $W \in \mathbb{R}_+^{t \times c}$ and $H^T \in \mathbb{R}_+^{v \times c}$ (we are using the transpose of H here for easier presentation below). In contrast to the approach based on Equation 3, the matrix factorization now contains a noise term $E \in \mathbb{R}^{t \times v}$ and allows negative values in the hidden layer N, which leads to the following model:

$$\hat{X} = T_\psi N + b_1 = T_\psi f(T_A X) + b_1 = T_\psi (WH^T + E) + b_1 \quad \text{(Eq 4)}$$

Additionally, the decomposition matrices (W and H) are expressed as random variables over which priors are expressed with parametric probability distributions. We use the likelihood assumption that each value in N is generated by the product of W and H assuming a Gaussian noise model $N(x|\mu, \tau^{-1})$ with mean $\mu$ and precision $\tau$ (precision being the inverse of variance):

$$N_{ij} \sim \kappa(N_{ij}|W_i H_j, \tau^{-1}) \quad \text{(Eq 5)}$$

where $W_i$ and $H_j$ denote the ith and jth rows of W and H respectively. The model parameters are denoted as $\theta = \{W, H, \tau\}$. One wants to choose prior distributions for the values of W, H and T to enforce certain properties of the decompositions such as non-negativity. One of many such approaches is to express a priori knowledge with an exponential prior distribution such as applied in [Brouwer et al., 2016, Schmidt et al., 2009]. For example, one may assume that the values of W and H independently follow exponential distributions with rate parameters $\lambda_{ik}^W$ and $\lambda_{jk}^H$ respectively:

$$W_{ik} \sim \varepsilon(W_{ik}|\lambda_{ik}^W); H_{ij} \sim \varepsilon(H_{jk}|\lambda_{jk}^H); \tau \sim G(\tau, \alpha, \beta) \quad \text{(Eq 6)}$$

The posterior distributions are obtained with Bayesian inference $p(D|\theta)p(\theta)$, although there is no exact analytical solution for these posterior distributions. There are two computational strategies to obtain an approximate solution for the posterior distributions. [Schmidt et al., 2009] proposed a Gibbs sampling algorithm for approximating the posterior distribution. [Brouwer et al., 2016] proposed Variational Bayes (VB), which utilises proxy distributions that factorise, assuming all parameters are independent. More details can be found in [Schmidt et al., 2009] for Gibbs sampling and in [Brouwer et al., 2016] for Variational Bayes.

9) Workflow Training

FIG. 1 is a high-level schematic diagram showing an overview of the process flow described herein for training and production (depicted in the top and bottom portions of FIG. 1 respectively). During the training phase, the system learns certain parameters from analysing a relatively large data set containing multiple scans. During a subsequent production phase, these learnt parameters, namely the deconvolution filter ($T_A$) and (or) the spatial maps (H) of the brain network components, are used to analyse smaller data sets, for example, individual scans. Note that neural time courses for the network components are obtained in both phases, however, the production phase can be applied to individual scans, whereas the training phase learns from a cohort of multiple scans. In addition, the production phase is able to execute much more quickly than the training phase (because the learnt parameters are already known).

During the training phase of FIG. 1 (top portion), for each task, all fMRI data for a reference cohort of n scans, each scan having a duration t and comprising v voxels, is concatenated in time and randomly masked to split the data into 70% training data and 30% test data (for example). The deconvolution filter ($T_A$) is learned to derive the (surrogate) neural activity in each voxel of the fMRI data, as per equations 1 and 2 above (see the left-hand portion of FIG. 1). The determination of ($T_A$) involves the inversion of the known Toeplitz matrix ($T_\psi$) under the constraints that neural surrogate values are positive (a neuro-biological constraint) and that multiplying $T_A$ and $T_\psi$ approximates the identity matrix.

(Note that the inversion of a Toeplitz matrix is a non-trivial and ill-posed problem with many non-deterministic possible solutions; the implementations described herein, see equations (1) and (2), utilise a neural network-based optimisation under positive constraints to perform the inversion. This technique is believed to differ from existing solutions in the literature, although such existing solutions might also be employed in other implementations of the overall approach described herein).

A non-negative matrix factorization (NMF) is then applied (see right-hand portion of FIG. 1) to find a compression into c neural activity time courses (W) and their respective spatial extents (or maps) (H), as per equation (3). A NMF cross-validation may be applied to obtain an optimal decomposition into $c_{opt}$ network components (maps) per task—in other words, finding an optimised number of components per task, which can be seen as the smallest number of components in H that supports an accurate representation of the neural activity for the task across the cohort.

10) Workflow Production

The lower portion of FIG. 1 illustrates a production context, after the training phase has been completed, with H and $T_A$ now known. The processing is shown for a single scan, and the BOLD data ($X_i$) is again transformed to a corresponding record ($N_i$) of neural activity. However, this transformation is now very fast (real-time) because $T_A$ is known (so it is a direct transformation from $X_i$ to $N_i$, without any optimisation). Likewise, the neural activity data ($N_i$) can be decomposed into $c_{opt}$ time courses for each of $c_{opt}$ respective network components, and this decomposition is again very fast (real-time) because H is known. Accordingly, in the production phase the neural activity estimate $W_i$ for a new subject $X_i$ can be derived in real-time using the trained deconvolution filter $T_A$ and the trained spatial maps H.

Figure 2:
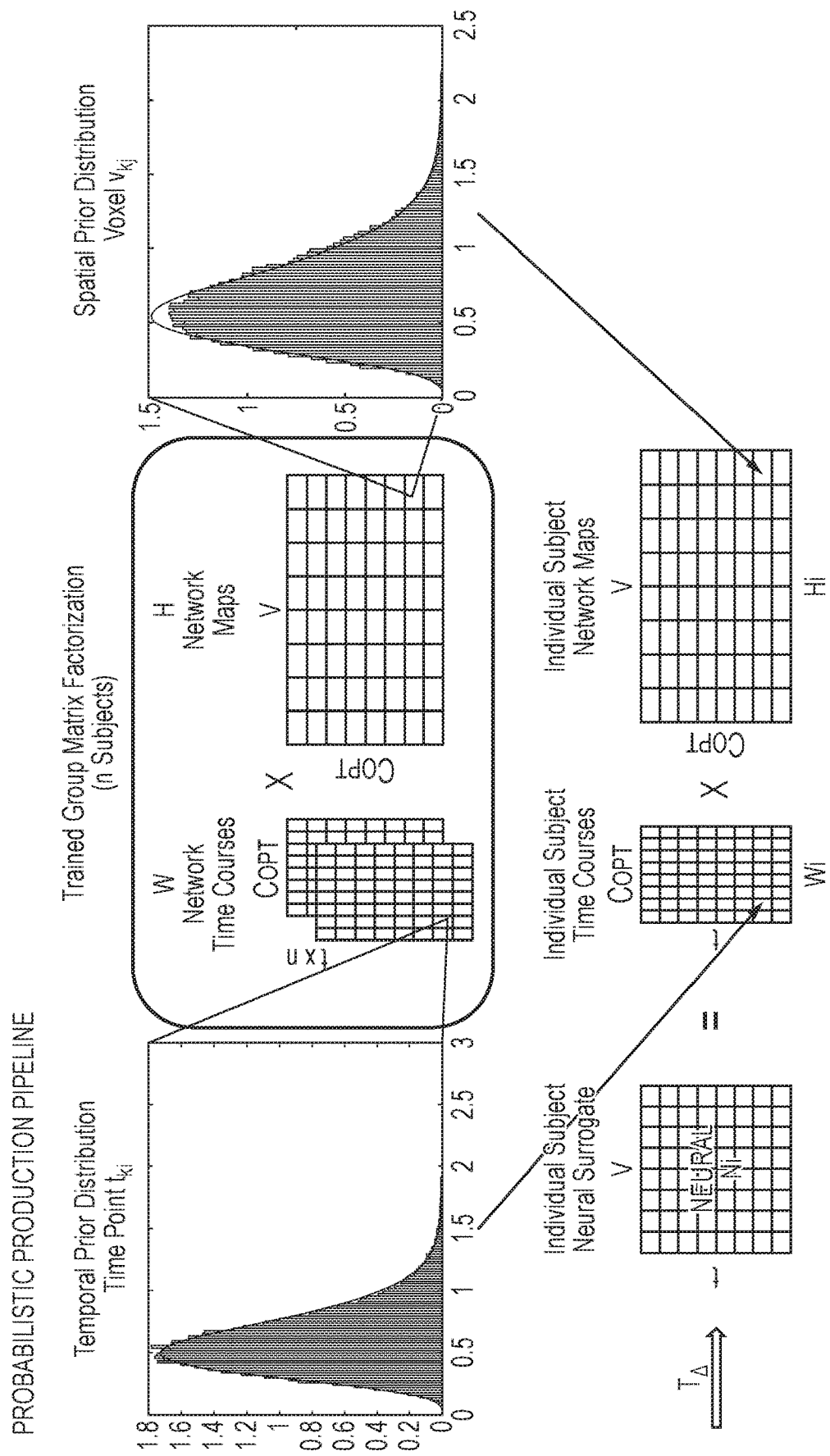
FIG. 2 is a schematic diagram showing the probabilistic approach for individual subject analysis during the production phase as described herein.

FIG. 2 shows a slight modification of the production processing of FIG. 1, adopting a probabilistic approach that allows $H_i$ to be different from H (as derived in the training phase) to provide increased flexibility. As depicted in FIG. 2, this approach assumes prior probability distributions over the individual elements in $W_i$ (temporal) and $H_i$ (spatial). The mean of each prior distribution for W and H respectively initialises the individual elements of $W_i$ and $H_i$. This approach again involves an optimisation, in effect trading off the likelihoods of $W_i$ and $H_i$ according to the priors against the fit to the data ($N_i$); however this approach also allows the uncertainty of the decomposition to be determined (how much variation can be accommodated in $W_i$ and $H_i$ while retaining an acceptable fit to the data).

It will be appreciated that once the training phase has been completed, the production pipeline of FIG. 1 or 2 can be used with as many different scans as desired, i.e. the training phase may be regarded as a one-off analysis to determine $T_A$ and H. However, if so desired the training phase may be performed again with additional or different data to confirm and refine the determined values of $T_A$ and H.

Note also that while FIGS. 1 and 2 are based on performing a deconvolution prior to a matrix decomposition (compression), as per equation (3), the training and/or production may also be implemented by performing the deconvolution after the matrix decomposition (compression), as per equation (3A). A further implementation may performing the deconvolution in conjunction with the matrix decomposition (compression) by using a suitable joint estimation procedure.

11) Results and Discussion

Figure 3:
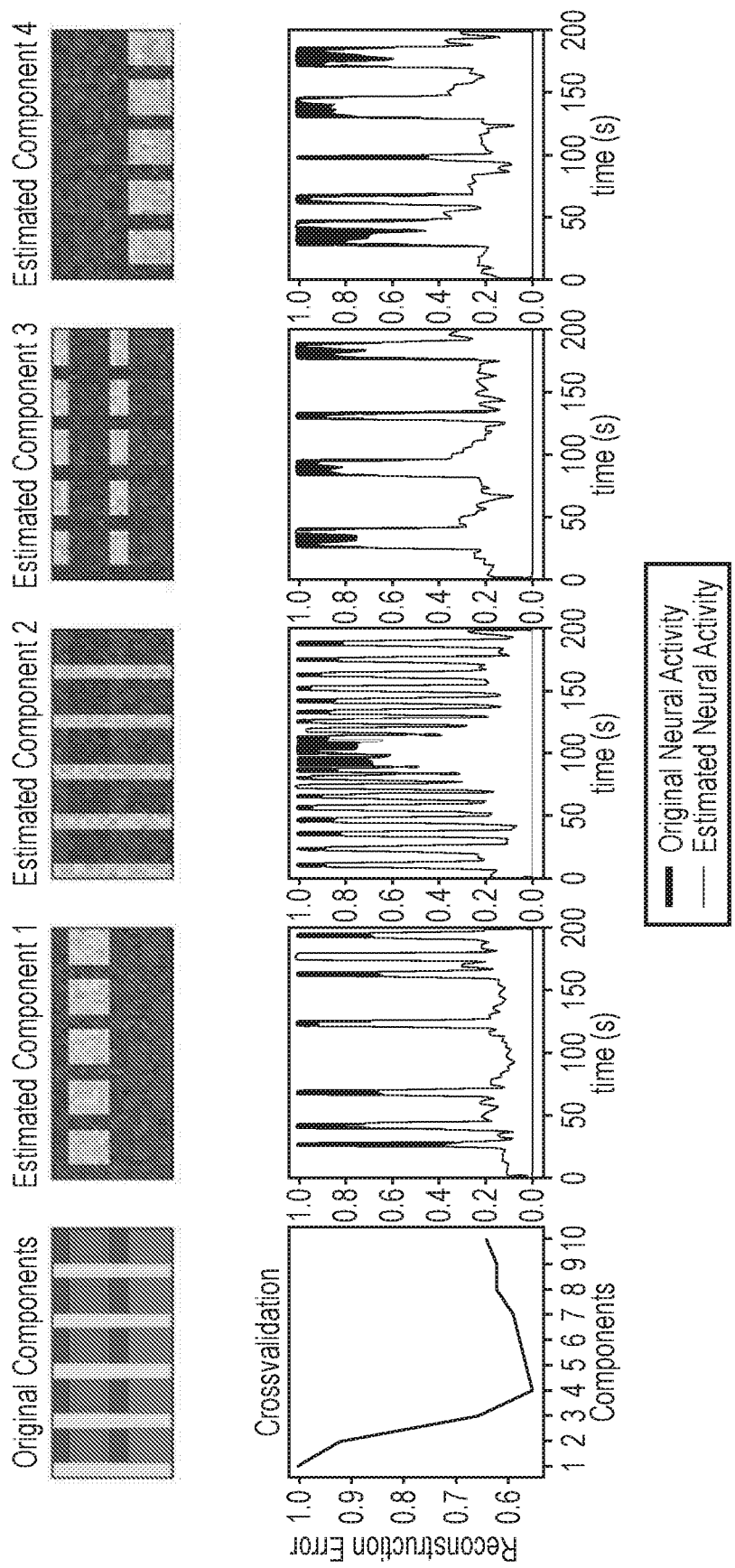
FIG. 3 illustrates results obtained from applying the approach described herein on simulated data.

FIG. 3 illustrates simulation data using 4 ground truth modeled spatial brain network components (first left in top row). These components are: five vertical bars, two horizontal bars (top and middle), an upper row of rectangles, and a lower row of rectangles. The estimated components, as derived using the approach described herein, are shown in the four other diagrams of the top row, which clearly reflect the four ground truth components. The cross-validation described in section 6 is seen to reach a minimum for the simulated data at 4 components (bottom first left)—in other words, adding further components does not improve the fit to the simulated data. The remainder of the bottom row shows the neural activation time course for each corresponding component (as shown above). In particular, the estimated time courses (shown in red) for each spatial map are a close approximation of the simulated original time courses (shown in black).

Figure 4:
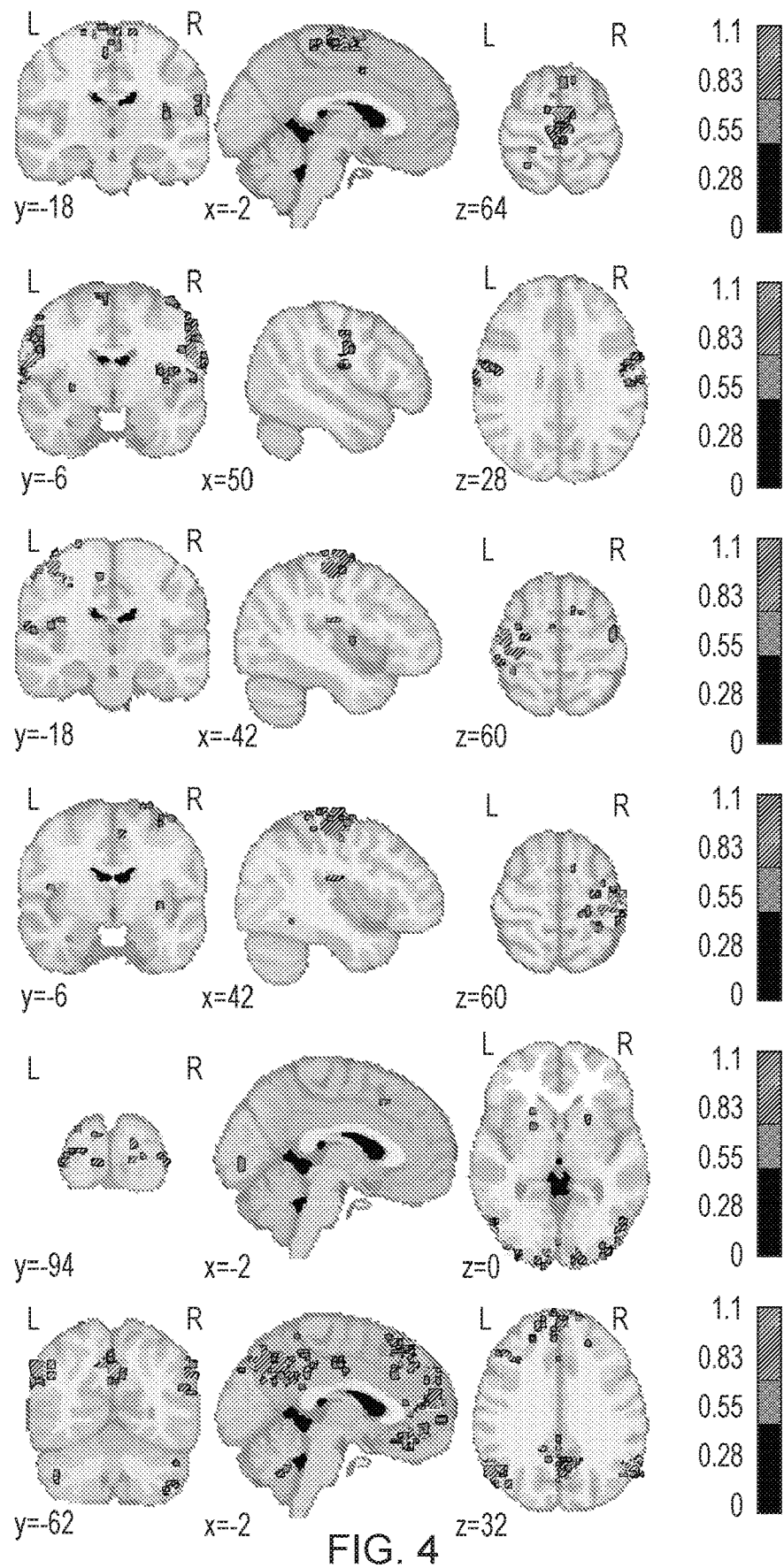
FIG. 4 illustrates results obtained from applying the approach described herein on single subject imaging data.
Figure 4:
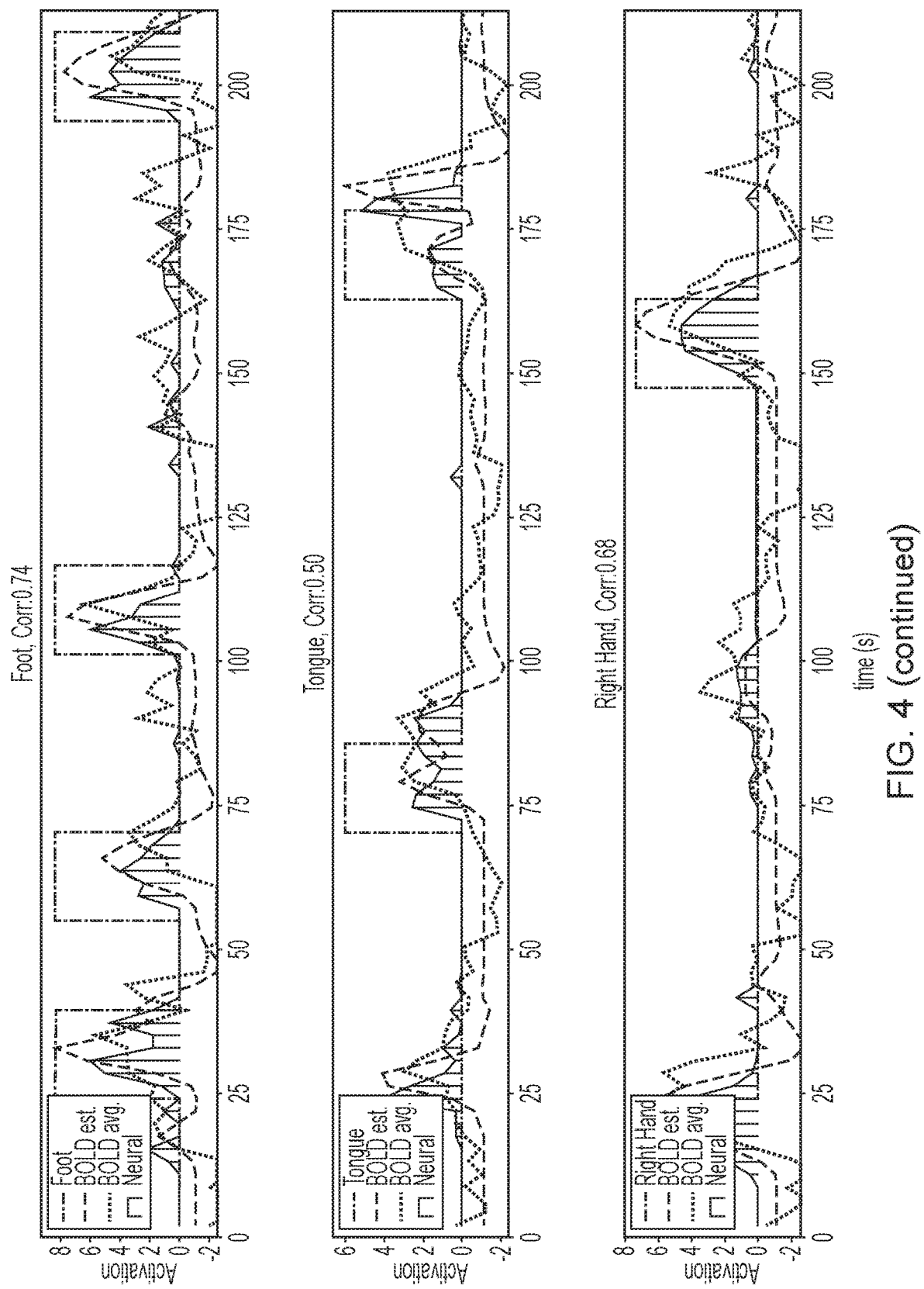
Figure 4:
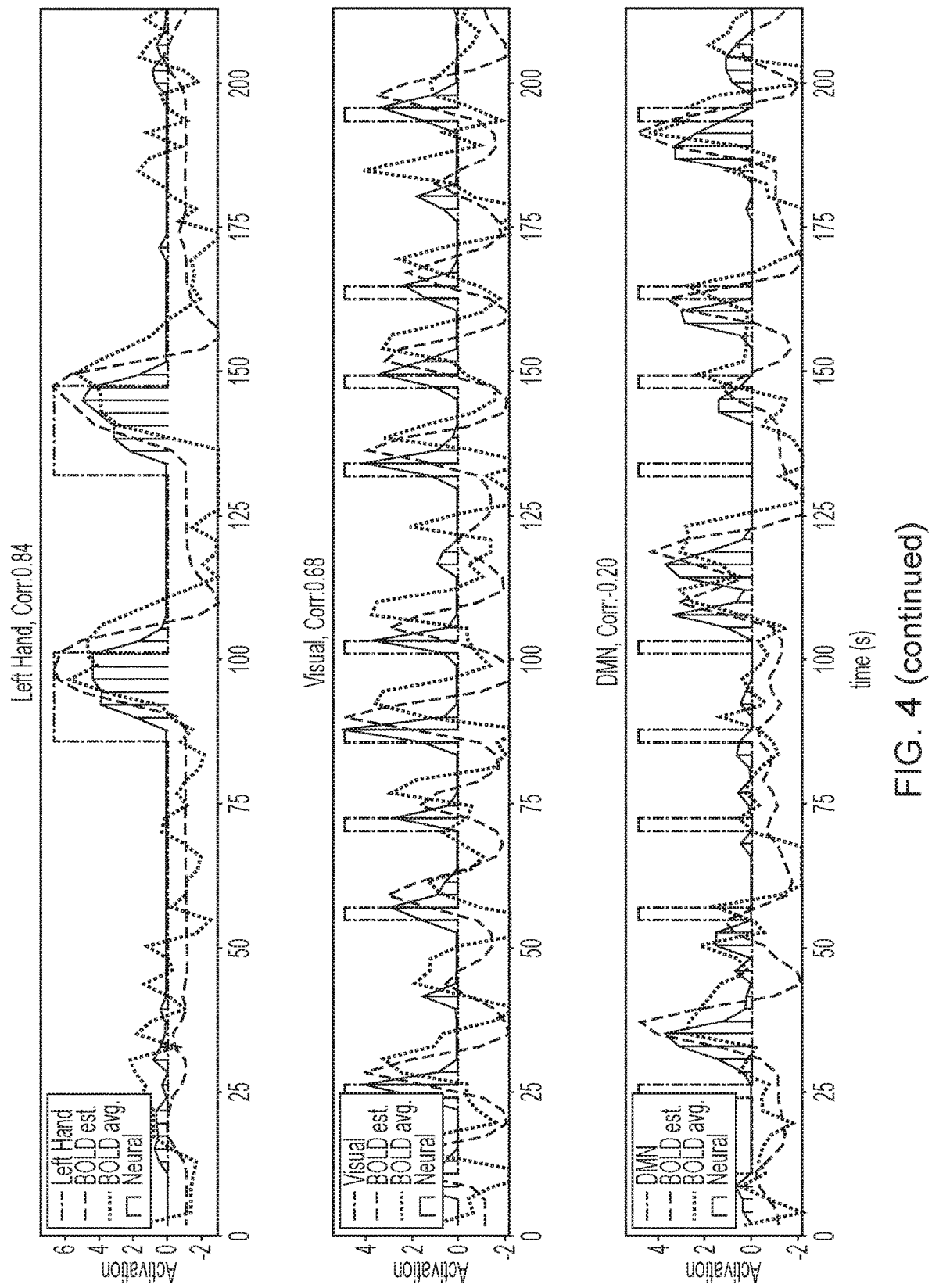

FIG. 4 illustrates brain networks (components), including their spatial map (distribution) on the left, and the activation time course for the corresponding components on the right. The spatial maps (patterns) of the network are shown in three views (coronal, sagittal and axial respectively). On the right are the corresponding time courses (sequences) for the networks, labelled with the nature of the performed movement actions during individual time slots throughout the scan. Thus the subjects are instructed by visual cues (sometimes referred to as the stimulus) during the scan to move respective body parts, such as foot movement, tongue movement, right hand movement, etc. The final row of FIG. 4 represents the default mode network (DMN). The blue line shows the time course of the presentation of the stimulus (which was not known to the algorithm). The red line represents the estimated surrogate neural time course within the spatial map of the brain component matching (associated with) the stimulus type and timing. The green solid line represents the estimated BOLD MRI time course within the component (such as obtained by applying the haemodynamic filter to the estimated surrogate neural time course as represented by the red line). The green dashed line represents the average observed BOLD time course within the spatial map of the brain network matching (associated with) the relevant stimulus timing and type. The corresponding spatial map for each of these five brain networks matches with what one would expect from literature, and known associations between brain function and location. The last row illustrated in FIG. 4 is the default mode (DFM); it can be seen that its surrogate neural activation time course is spontaneous and unrelated to any of the extrinsic tasks.

More particularly, the first four rows of FIG. 4 represent activated brain regions that belong to the Sensory-Motor (SMN) network and relate to stimuli of the foot, tongue, and left and right hand stimuli, respectively. Note that the stimulus (motor task) for these features has a block design. The fifth and sixth rows of FIG. 4 represent activated brain regions that correspond to the Visual Network (VN) and the Default Mode Network (DMN), respectively. The first five networks (corresponding to the first five rows) follow the respective block stimuli or visual cues given during the task. In contrast, the DMN network exhibits a neural activation profile unrelated to the task being performed, but remains strongly detectable.

The approach described herein for identifying surrogate neural activation time courses, and their subsequent compression into brain networks, using fMRI scans was compared to the currently only existing tool with similar functionality, Total Activation (TA), described in [Karahanoğlu et al., 2013]. The approach described herein was implemented in a GPU-based neural network framework (see https://www.tensorflow.org/) and runs (processes) approximately 100 scans in 5 hours. In contrast, the approach described in [Karahanoğlu et al., 2013] runs one scan in approximately 5 hours (information taken from the respective reference).

The approach described herein has broad applicability to the subject-wise analysis of resting state (and task-based) fMRI data for the brain. The technique avoids the introduction of artefacts by smoothing—note that the single-subject decompositions in FIG. 3 are spatially smooth, despite the fact that no spatial smoothing (or any other direct form of spatial regularization in contrast to [Karahanoğlu et al., 2013]) was used in the estimation process for the single subject. This lack of smoothing helps to avoid limitations found in existing techniques for the analysis of task-based and resting-state fMRI. Nevertheless, the technique described herein, which utilises advanced machine learning, is still able to reveal networks even for individual subjects. Accordingly, the approach described herein utilises a neural network framework to produce functional network decompositions for individual subjects without spatial smoothing. This approach can be applied at both a group level and and an individual level. It has the capability to provide single subject functional network representations, which in turn can reveal network differences, at the level of individuals, between healthy controls and individuals diagnosed with a given pathology. In addition, brain network estimates can be modelled with probability distributions instead of estimates, thereby producing uncertainty intervals for these probabilities, and so helping to identify brain networks that can reliably be reproduced.

The approach described herein may be implemented using a computer program, which may be provided on a non-transitory computer readable storage medium, such as an optical disk (CD or DVD) or flash memory. The computer program may be loaded into the memory from such a storage medium, or may be downloaded into the memory over a network, such as the Internet, for execution by the processor(s) to perform the method described herein. In some cases the processing may be implemented on a conventional general purpose computer running such a computer program; other implementations may use more specific hardware, e.g. an ASIC or GPU, or dedicated hardware, for implementing at least some the processing described herein. In some cases the functionality described herein may be incorporated into an fMRI system (apparatus), which is therefore able both to acquire MRI images, and also to subsequently analyse such acquired images as described herein.

Although various implementations and embodiments have been described herein, it will be appreciated that these are presented by way of example only, and that various modifications and adaptions of such implementations will be apparent to the skilled person according to the circumstances of any given implementation. Accordingly, the present invention is not limited to the specific implementations and embodiments described herein, but rather is defined by the appended claims and their equivalents.

REFERENCES

[Brouwer et al., 2016] Brouwer, T., Frellsen, J., and Lio, P. (2016). Fast bayesian non-negative matrix factorisation and tri-factorisation. arXiv preprint arXiv:1610.08127.

[Cichocki and Anh-Huy, 2009] Cichocki, A. and Anh-Huy, P. (2009). Fast local algorithms for large scale nonnegative matrix and tensor factorizations. IEICE transactions on fundamentals of electronics, communications and computer sciences, 92(3):708-721.

[Daubechies et al., 2009] Daubechies, I., Roussos, E., Takerkart, S., Benharrosh, M., Golden, C., D'ardenne, K., Richter, W., Cohen, J., and Haxby, J. (2009). Independent component analysis for brain fmri does not select for independence. Proceedings of the National Academy of Sciences, 106(26):10415-10422.

[Glorot and Bengio, 2010] Glorot, X. and Bengio, Y. (2010). Understanding the difficulty of training deep feedforward neural networks. In Proceedings of the Thirteenth International Conference on Artificial Intelligence and Statistics, pages 249-256.

[Gordon et al., 2017] Gordon, E. M., Laumann, T. O., Gilmore, A. W., Newbold, D. J., Greene, D. J., Berg, J. J., Ortega, M., Hoyt-Drazen, C., Gratton, C., Sun, H., et al. (2017). Precision functional mapping of individual human brains. Neuron, 95(4):791-807.

[Kanagal and Sindhwani, 2010] Kanagal, B. and Sindhwani, V. (2010). Rank selection in low-rank matrix approximations: A study of cross-validation for nmfs. In Proc Conf Adv Neural Inf Process, volume 1, pages 10-15.

[Karahanoğlu et al., 2013] Karahanoğlu, F. I., Caballero-Gaudes, C., Lazeyras, F., and Van De Ville, D. (2013). Total activation: fmri deconvolution through spatio-temporal regularization. Neuroimage, 73:121-134.

[Logothetis et al., 2001] Logothetis, N. K., Pauls, J., Augath, M., Trinath, T., and Oeltermann, A. (2001). Neurophysiological investigation of the basis of the fmri signal. Nature, 412(6843):150-157.

[Logothetis and Wandell, 2004] Logothetis, N. K. and Wandell, B. A. (2004). Interpreting the bold signal. Annu. Rev. Physiol., 66:735-769.

[Orfanos et al., 2017] Orfanos, D. P., Michel, V., Schwartz, Y., Pinel, P., Moreno, A., Le Bihan, D., and Frouin, V. (2017). The brainomics/localizer database. NeuroImage, 144:309-314.

[Pinel et al., 2012] Pinel, P., Fauchereau, F., Moreno, A., Barbot, A., Lathrop, M., Zelenika, D., Le Bihan, D., Poline, J.-B., Bourgeron, T., and Dehaene, S. (2012). Genetic variants of foxp2 and kiaa0319/ttrap/them2 locus are associated with altered brain activation in distinct language-related regions. Journal of Neuroscience, 32(3): 817-825.

[Pinel et al., 2007] Pinel, P., Thirion, B., Meriaux, S., Jobert, A., Serres, J., Le Bihan, D., Poline, J.-B., and Dehaene, S. (2007). Fast reproducible identification and large-scale databasing of 295 individual functional cognitive networks. BMC neuroscience, 8(1):91

[Schmidt et al., 2009] Schmidt, M. N., Winther, O., and Hansen, L. K. (2009). Bayesian nonnegative matrix factorization. In International Conference on Independent Component Analysis and Signal Separation, pages 540-547. Springer.

The invention claimed is:

1. A method for analysing a functional magnetic resonance imaging (fMRI) scan representing a time-sequence, comprising t time points, of images comprising v voxels, where each scan can be represented by a data matrix $X \in \mathbb{R}^{t \times v}$ the method comprising:
   modelling the scan data X as the convolution of a neural activation time course $N \in \mathbb{R}_+^{t \times v}$ and a haemodynamic filter $\Psi$, and performing an inverse operation to estimate N from X and $\Psi$; and
   decomposing the neural activation time course N into multiple brain network components by representing N as the product of a first matrix H defining, for each component, a spatial map of the voxels belonging to that component, and a second matrix W defining, for each component, the time sequence of activation of that component during the scan.

2. The method of claim 1, wherein decomposing the neural activation comprises a non-negative matrix factorisation.

3. The method of claim 1, further comprising adopting a probabilistic approach for decomposing the neural activation time course into multiple brain network components by defining prior probability distributions over individual elements in W and H.

4. The method of claim 3, further comprising using the prior probability distributions to estimate an uncertainty associated with the individual elements in W and H.

5. A method for analysing a functional magnetic resonance imaging (fMRI) scan representing a time-sequence, comprising t time points, of images comprising v voxels, where each scan can be represented by a data matrix $X \in \mathbb{R}^{t \times v}$ the method comprising:
   decomposing the data matrix X into multiple brain network components by representing X as the product of a first matrix H defining, for each component, a spatial map of the voxels belonging to that component, and a second matrix W*, where W* is formed by convolving a haemodynamic filter with a third matrix N*, defining, for each component, the time sequence of activation of that component during the scan; and
   performing an inverse operation to estimate N* from W*.

6. The method of claim 5, wherein decomposing the data matrix comprises a matrix factorisation.

7. The method of claim 1, wherein the inverse operation comprises a nonlinear deconvolution.

8. The method of claim 1, wherein the inverse operation and/or the matrix H are known.

9. The method of claim 1, further comprising determining the inverse operation and/or the matrix H during a training phase, based on analysing a cohort of multiple scans.

10. The method of claim 9, wherein the inverse operation is determined during the training phase by minimising, for the cohort of scans, differences between (i) the observed data X; and (ii) reconstructed data $\hat{X}$.

11. The method of claim 10, wherein the reconstructed data is generated by applying a trial inverse operation to the observed data followed by the haemodynamic filter and performing an optimisation to determine a trial inverse operation that minimises said differences and that is then used as the inverse operation.

12. The method of claim 9, wherein during the training phase, the matrix H is consistent across the cohort of multiple scans.

13. The method of claim 12, wherein determining the matrix H includes determining the smallest number of components of H such that WH corresponds to N or W*H corresponds to X across the cohort of multiple scans.

14. The method of claim 13, wherein determining the smallest number of components is performed using a cross-validation technique.

15. The method of claim 9, wherein the cohort of multiple scans all relate to a specific task.

16. The method of claim 1, further comprising preprocessing each fMRI scan to perform motion alignment.

17. The method of claim 1, further comprising preprocessing each fMRI scan to perform co-registration with a structural scan so as to relate functional and anatomical brain regions.

18. The method of claim 1, further comprising acquiring said fMRI scan.

19. Apparatus for analysing a functional magnetic resonance imaging (fMRI) scan representing a time-sequence, comprising t time points, of images comprising v voxels, where each scan can be represented by a data matrix $X \in \mathbb{R}^{t \times v}$ the apparatus including a computer processing system configured to:
   model the scan data X as the convolution of a neural activation time course $N \in \mathbb{R}_+^{t \times v}$ and a haemodynamic filter $\Psi$, and
   perform an inverse operation with respect to $\Psi$ and a matrix decomposition into multiple brain network components using a matrix H defining, for each component, a spatial map of the voxels belonging to that component, to derive for each component, the time sequence of activation of that component during the scan.

* * * * *

UNITED STATES PATENT AND TRADEMARK OFFICE
CERTIFICATE OF CORRECTION

PATENT NO. : 11,867,783 B2
APPLICATION NO. : 17/058714
DATED : January 9, 2024
INVENTOR(S) : Michael Hutel and Sebastien Ourselin It is certified that error appears in the above-identified patent and that said Letters Patent is hereby corrected as shown below:

In the Claims

In Claim 5, Column 16, Line 1, after "haemodynamic filter" please insert --$\Psi$--.

In Claim 11, Column 16, Line 20, after "haemodynamic filter" please insert --$\Psi$--.

Signed and Sealed this
Twelfth Day of March, 2024

*Katherine Kelly Vidal*
Katherine Kelly Vidal
*Director of the United States Patent and Trademark Office*